United States Patent
Bharmi et al.

(10) Patent No.: US 8,706,239 B2
(45) Date of Patent: Apr. 22, 2014

(54) SYSTEMS AND METHODS FOR CONTROLLING NEUROSTIMULATION BASED ON REGIONAL CARDIAC PERFORMANCE FOR USE BY IMPLANTABLE MEDICAL DEVICES

(75) Inventors: Rupinder Bharmi, Canyon Country, CA (US); Taraneh Ghaffari Farazi, San Jose, CA (US); Ryan Rooke, La Mesa, CA (US); Stuart Rosenberg, Castaic, CA (US); Kritika Gupta, Sunnyvale, CA (US); Riddhi Shah, San Jose, CA (US); Gene A. Bornzin, Simi Valley, CA (US); Wenbo Hou, Valencia, CA (US); Laurence S. Sloman, West Hollywood, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/485,404

(22) Filed: May 31, 2012

(65) Prior Publication Data

US 2013/0325083 A1    Dec. 5, 2013

(51) Int. Cl.
*A61N 1/00* (2006.01)

(52) U.S. Cl.
USPC ........................................................... 607/46

(58) Field of Classification Search
USPC .................................................. 607/46, 9
See application file for complete search history.

(56) References Cited

U.S. PATENT DOCUMENTS

| | | | |
|---|---|---|---|
| 5,549,650 A | 8/1996 | Bornzin et al. | |
| 5,891,176 A | 4/1999 | Bornzin | |
| 6,058,328 A | 5/2000 | Levine et al. | |
| 6,134,472 A | 10/2000 | Strandberg et al. | |
| 6,314,323 B1 | 11/2001 | Ekwall | |
| 6,937,896 B1 * | 8/2005 | Kroll | 607/9 |
| 7,099,718 B1 | 8/2006 | Thacker et al. | |
| 7,139,609 B1 | 11/2006 | Min et al. | |
| 7,149,584 B1 | 12/2006 | Koh et al. | |
| 7,164,944 B1 | 1/2007 | Kroll et al. | |
| 7,207,947 B2 | 4/2007 | Koh et al. | |
| 7,627,374 B1 | 12/2009 | Farazi et al. | |
| 7,632,235 B1 | 12/2009 | Karicherla et al. | |

(Continued)

FOREIGN PATENT DOCUMENTS

| | | |
|---|---|---|
| WO | 2007064924 A1 | 6/2007 |
| WO | 2007064936 A1 | 6/2007 |

OTHER PUBLICATIONS

Ardell, Jeffrey L. et al., "Dorsal spinal cord stimulation obtunds the capacity of intrathoracic extracardiac neurons to transduce myocardial ischemia," Am. J. Physiol., Regul Integr Comp Physiol. 2009;297:R470-R477.

(Continued)

*Primary Examiner* — Christopher D Koharski
*Assistant Examiner* — Nadia Ahmad

(57) ABSTRACT

Techniques are provided for controlling neurostimulation such as spinal cord stimulation (SCS) using a cardiac rhythm management device (CRMD). In various examples described herein, neurostimulation is delivered to a patient while regional cardiac performance of the heart of the patient is assessed by the CRMD. The delivery of further neurostimulation is adjusted or controlled based, at least in part, on the regional cardiac performance, preferably to enhance positive effects on the heart due to the neurostimulation or to mitigate any negative effects. Regional cardiac performance is assessed based on parameters derived from cardiogenic impedance signals detected along various vectors through the heart.

19 Claims, 9 Drawing Sheets

(56) References Cited

U.S. PATENT DOCUMENTS

| | | | |
|---|---|---|---|
| 7,711,415 | B1 | 5/2010 | Farazi et al. |
| 7,769,441 | B2 | 8/2010 | Foreman et al. |
| 7,826,899 | B1 | 11/2010 | Ryu et al. |
| 7,860,563 | B2 | 12/2010 | Foreman et al. |
| 7,925,347 | B1 | 4/2011 | Bornzin |
| 7,957,797 | B2 | 6/2011 | Bourget et al. |
| 8,016,764 | B1 | 9/2011 | Shelchuk |
| 8,019,409 | B2 | 9/2011 | Rosenberg et al. |
| 2007/0129774 | A1 | 6/2007 | Bourget et al. |
| 2007/0150026 | A1 | 6/2007 | Bourget et al. |
| 2007/0150029 | A1 | 6/2007 | Bourget et al. |
| 2009/0187087 | A1 | 7/2009 | Turcott |
| 2010/0057158 | A1 | 3/2010 | Rodriguez et al. |
| 2010/0114228 | A1 | 5/2010 | Bharmi et al. |
| 2010/0152801 | A1 | 6/2010 | Koh et al. |
| 2010/0161006 | A1 | 6/2010 | Keel et al. |
| 2010/0331921 | A1 | 12/2010 | Bornzin et al. |
| 2011/0066055 | A1 | 3/2011 | Bharmi et al. |
| 2011/0082522 | A1 | 4/2011 | Bourget et al. |
| 2011/0224555 | A1 | 9/2011 | Park |

OTHER PUBLICATIONS

Bocchiardo, Mario et al., "Intracardiac impedance monitors stroke volume in resynchronization therapy patients," Europace. 2010;12:702-707.

Bocchiardo, Mario et al., "Resynchronization therapy optimization by intracardiac impedance," Europace. 2010;12:1589-1595.

DeJongste, Mike J.L., "Spinal cord stimulation for ischemic heart disease," Neurol Res. 2000; 22(3):293-298.

Foreman, Robert D. et al. "Modulation of intrinsic cardiac neurons by spinal cord stimulation: implications for its therapeutic use in angina pectoris," Cardiovasc Res. 2000;47(2):367-375.

Issa, Ziad F. et al., "Thoracic Spinal Cord Stimulation Reduces the Risk of Ischemic Ventricular Arrhythmias in a Postinfarction Heart Failure Canine Model," Circulation. 2005;111(24):3217-3220.

Lopshire, John C. et al., "Spinal Cord Stimulation Improves Ventricular Function and Reduces Ventricular Arrhythmias in a Canine Postinfarction Heart Failure Model," Circulation. 2009;120:286-294.

Olgin, Jeffrey E. MD et al., "Effects of Thoracic Spinal Cord Stimulation on Cardiac Autonomic Regulation of the Sinus and Atrioventricular Nodes," J Cardiovasc Electrophysiol. 2002;13(5):475-481.

Sanderson, J.E. et al., "Spinal electrical stimulation for intractable angina—long-term clinical outcome and safety," Eur Heart J. 1994;15(6):810-814.

Stahl, Carsten MD et al., "Assessing Acute Ventricular Volume Changes by Intracardiac Impedance in a Chronic Heart Failure Animal Model" PACE 2009;32:1395-1401.

Zima, Endre et al., "Determination of left ventricular volume changes by intracardiac conductance using a biventricular electrode configuration," Europace. 2006;8:537-544.

\* cited by examiner

PARAMETER CONFIGURATION MULTIDIMENSIONAL SET

| PARAMETER | FREQ | AMP | PULSE WIDTH | ELECTRODE | DURATION |
|---|---|---|---|---|---|
| 1 | | | | | |
| 2 | | | | | |
| ..... | | | | | |
| N | | | | | |

$205_1$ ... $205_N$, $213$

IMPEDANCE VECTOR #1

| PARAMS. | FIDUCIAL POINT CHANGES | dZ/dt | CORRELATION BETWEEN Zc VALUES | ELECTRO-MECHANICAL DELAY | IEGM-Zc FIDUCIAL POINT | ELECTRODE MOTION AS A MEASURE OF DYSSYNCHRONY | CO |
|---|---|---|---|---|---|---|---|
| 1 | | | | | | | |
| 2 | | | | | | | |
| ..... | | | | | | | |
| N | | | | | | | |

$219_1$ ... $219_N$, $217_1$

IMPEDANCE VECTOR #2

| PARAMS. | FIDUCIAL POINT CHANGES | dZ/dt | CORRELATION BETWEEN Zc VALUES | ELECTRO-MECHANICAL DELAY | IEGM-Zc FIDUCIAL POINT | ELECTRODE MOTION AS A MEASURE OF DYSSYNCHRONY | CO |
|---|---|---|---|---|---|---|---|
| 1 | | | | | | | |
| 2 | | | | | | | |
| ..... | | | | | | | |
| N | | | | | | | |

$221_1$ ... $221_N$, $217_2$

IMPEDANCE VECTOR N

| PARAMS. | FIDUCIAL POINT CHANGES | dZ/dt | CORRELATION BETWEEN Zc VALUES | ELECTRO-MECHANICAL DELAY | IEGM-Zc FIDUCIAL POINT | ELECTRODE MOTION AS A MEASURE OF DYSSYNCHRONY | CO |
|---|---|---|---|---|---|---|---|
| 1 | | | | | | | |
| 2 | | | | | | | |
| ..... | | | | | | | |
| N | | | | | | | |

SYSTEMS AND METHODS FOR CONTROLLING NEUROSTIMULATION BASED ON REGIONAL CARDIAC PERFORMANCE FOR USE BY IMPLANTABLE MEDICAL DEVICES

FIELD OF THE INVENTION

The invention generally relates to implantable cardiac rhythm management devices (CRMDs) and implantable neurostimulation devices and, in particular, to techniques for controlling spinal cord stimulation (SCS) based on regional cardiac performance assessed using a CRMD.

BACKGROUND OF THE INVENTION

SCS is a type of neurostimulation intended to manage chronic pain, particularly within the back, neck, arms or legs, particularly neuropathic pain, i.e. pain marked by burning, tingling or numbness. Benefits of SCS or other forms of neurostimulation may include: a reduction in pain; a reduction or elimination of the use of pain medications; and increased activity levels and an improved overall quality of life. Neurostimulation has been used to manage pain that comes from failed back surgery syndrome (FBSS) or post-laminectomy syndrome and other neuropathies. Neurostimulation operates by intercepting pain signals before they reach the brain. To this end, a small SCS system may be implanted within the body to deliver electrical pulses to nerves along the spinal cord. Some patients describe the resulting sensation as a gentle massaging sensation or, in some cases, simply the absence of pain. The SCS system typically includes a small generator device, similar to a pacemaker, equipped to send electrical pulses to leads mounted along the nerves near the spinal cord. The generator is usually implanted in the abdomen or buttock area. The stimulation leads include either thin wires or paddles for delivering pulses from the generator to the nerves along the spinal cord. Thin wire leads, also referred to as percutaneous leads, are implanted within the epidural space using a special needle. Paddle leads are instead typically implanted during a surgical procedure where a small amount of bone is removed from one of the vertebra. An external programmer device, similar to a remote control, is provided to allow the patient to control or adjust the stimulation.

SCS is an approved treatment for chronic pain and intractable angina pectoris. Preclinical and clinical studies have shown that SCS has cardioprotective effects. Long term SCS has been shown to protect against ventricular arrhythmias and also improve left ventricular function. See, for example, DeJongste, "Spinal cord stimulation for ischemic heart disease" Neurol Res 2000; 22(3):293-298; Sanderson et al., "Spinal electrical stimulation for intractable angina—long-term clinical outcome and safety" Eur Heart J 1994; 15(6):810-814; Foreman et al. "Modulation of intrinsic cardiac neurons by spinal cord stimulation: implications for its therapeutic use in angina pectoris" Cardiovasc Res 2000; 47(2):367-375; Olgin et al., "Effects of Thoracic Spinal Cord Stimulation on Cardiac Autonomic Regulation of the Sinus and Atrioventricular Nodes" J Cardiovasc Electrophysiol 2002; 13(5):475-481; Issa et al., "Thoracic Spinal Cord Stimulation Reduces the Risk of Ischemic Ventricular Arrhythmias in a Postinfarction Heart Failure Canine Model" Circulation 2005; 111(24):3217-3220; and Lopshire et al., "Spinal Cord Stimulation Improves Ventricular Function and Reduces Ventricular Arrhythmias in a Canine Postinfarction Heart Failure Model" Circulation 2009; 120:286-294. Numerous other papers discussing the effects of SCS on cardiac disorders are available in the medical literature.

Generally, SCS can have positive or negative effects including differing regional effects within various heart tissues and chambers. Accordingly, it would be desirable to control the operation of the SCS device (or other neurostimulation device) to enhance any positive effects and to eliminate or mitigate any negative effects, preferably on a regional basis. Patients with implantable SCS devices may also have CRMDs implanted therein such as pacemakers, implantable cardioverter/defibrillators (ICDs) and cardiac resynchronization therapy devices (CRTs). Accordingly, it would be particularly desirable to provide techniques for allowing the CRMD to assess any regional effects on the heart arising due to SCS and to then adjust SCS therapy so as to enhance positive effects and eliminate or mitigate negative effects. It is to this end that various aspects of the invention are generally directed.

SUMMARY OF THE INVENTION

In an exemplary embodiment, a method is provided for use with an implantable medical system wherein the system includes a CRMD and a neurostimulation device. Briefly, neurostimulation is delivered to the patient using the neurostimulation device while regional cardiac performance is assessed using the CRMD. The delivery of neurostimulation is then adjusted or controlled based, at least in part, on the regional cardiac performance, preferably to enhance positive effects on the heart due to the neurostimulation and to eliminate or mitigate any negative effects.

In an illustrative embodiment, the CRMD is a pacemaker, ICD, CRT or similar device and the neurostimulation device is an SCS device. To assess the regional effects of neurostimulation on the heart, SCS is controlled to adjust various neuromodulation parameters through ranges of programmable values while the CRMD concurrently assess regional cardiac performance. Regional cardiac performance is assessed based on changes in hemodynamics measured using cardiogenic impedance measured along various vectors using cardiac pacing/sensing leads such as a right atrial (RA) lead, right ventricular (RV) lead and a left ventricular/coronary sinus (LV/CS) lead. The CRMD then maps SCS neuromodulation parameters to regional cardiac performance to thereby assess the effect of different SCS neuromodulation parameters on regional cardiac performance. A set of optimal neuromodulation parameters are then identified that tend to improve cardiac performance (regionally and/or globally) while mitigating or eliminating any adverse effects arising due to SCS. Thereafter, SCS is preferably delivered using the optimal neuromodulation parameters, subject to modification by the patient if needed to improve pain management. Insofar as impedance is concerned, it should be understood that related electrical parameters might be detected and/or exploited instead, such as admittance, conductance or immittance. Those skilled in the art can convert among these related parameters as needed. Herein, "impedance" is intended to generally include any related electrical parameters such as admittance, conductance and immittance.

In one example, the set of neuromodulation parameters to be adjusted includes: the neuromodulation amplitude; the neuromodulation frequency; the neuromodulation pulse width; the neuromodulation electrode configuration and the neuromodulation duration. The impedance vectors used by the CRMD to assess regional cardiac performance based on cardiogenic impedance include various large field vectors; narrow field vectors; bipolar vectors; tripolar vectors; and/or quadpolar vectors. To assess cardiac performance based on the impedance signals, the CRMD detects and evaluates a set of fiducial points within each cardiac cycle such as the maximum of the cardiogenic impedance (Zc max); the minimum of the cardiogenic impedance (Zc min) and the maximum positive rate of change of the cardiogenic impedance (dZc/dt max). These fiducial points/impedance features are then used to estimate hemodynamic measures e.g. cardiac output. The device then evaluates regional differences in cardiac performance based on, for example, the degree of homogeneity among the plurality of cardiogenic impedance signals, where a greater degree of homogeneity is generally deemed to be advantageous. Homogeneity may be assessed, for example, based on a comparison of changes in the fiducial points or by a degree of correlation among the plurality of cardiogenic impedance signals.

Still further, various electromechanical delay values may be determined from a comparison of cardiogenic impedance signals and concurrent intracardiac electrogram (IEGM) signals. Electromechanical delay values corresponding to different sensing vectors are then compared to assess homogeneity. As another example, cardiac dyssynchrony is assessed based on electrode motion detected from the cardiogenic impedance signals, which is then used to evaluate homogeneity. Additionally, various techniques may be used to determine or estimate cardiac output (CO) to gain a measure of cardiac performance, either regionally or globally. Preferably, each of the various cardiac performance parameters is mapped to neuromodulation parameters so that the device can identify an optimal set of neuromodulation parameters, which is then used to control the delivery of further SCS. Also, preferably, the mapping is performed for various patient postures and subject to various diurnal variations, allowing the device to identify a particular set of preferred or optimal neuromodulation parameters for each posture and for different times of the day.

Method and system examples are described in detail below.

BRIEF DESCRIPTION OF THE DRAWINGS

The above and further features, advantages and benefits of the invention will be apparent upon consideration of the descriptions herein taken in conjunction with the accompanying drawings, in which:

FIGS. 3-1 and 3-2 illustrates an exemplary embodiment of the general technique of FIG. 2, wherein the neurostimulation is SCS;

FIG. 4 illustrates tables/maps used by the technique of FIGS. 3-1 and 3-2 that relate SCS control parameters to corresponding cardiac performance parameters measured along various vectors to assess regional cardiac performance;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of CRMD/SCS System

Figure 1:
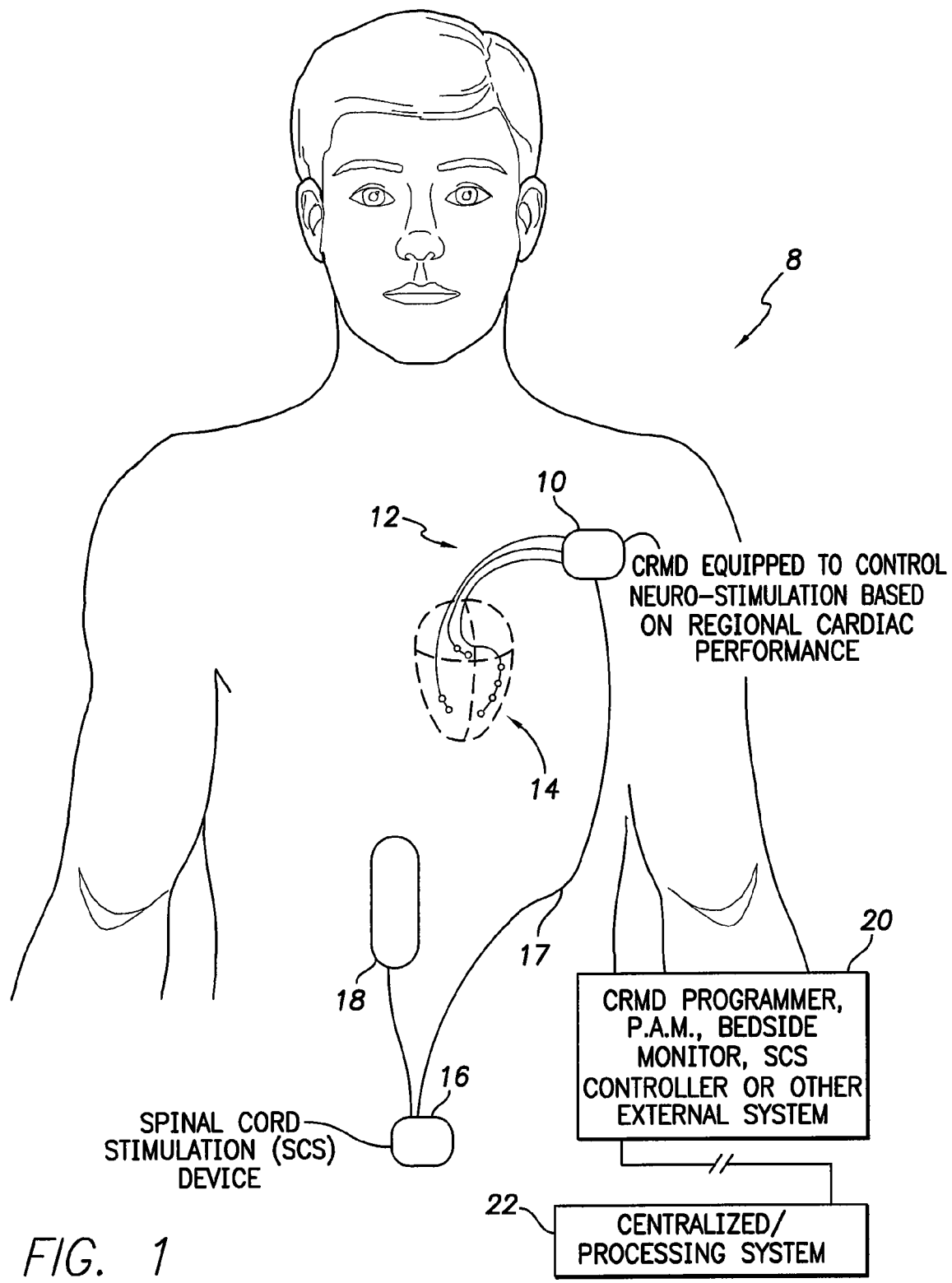
FIG. 1 illustrates pertinent components of a CRMD equipped to control neurostimulation based on regional cardiac performance.
Figure 7:
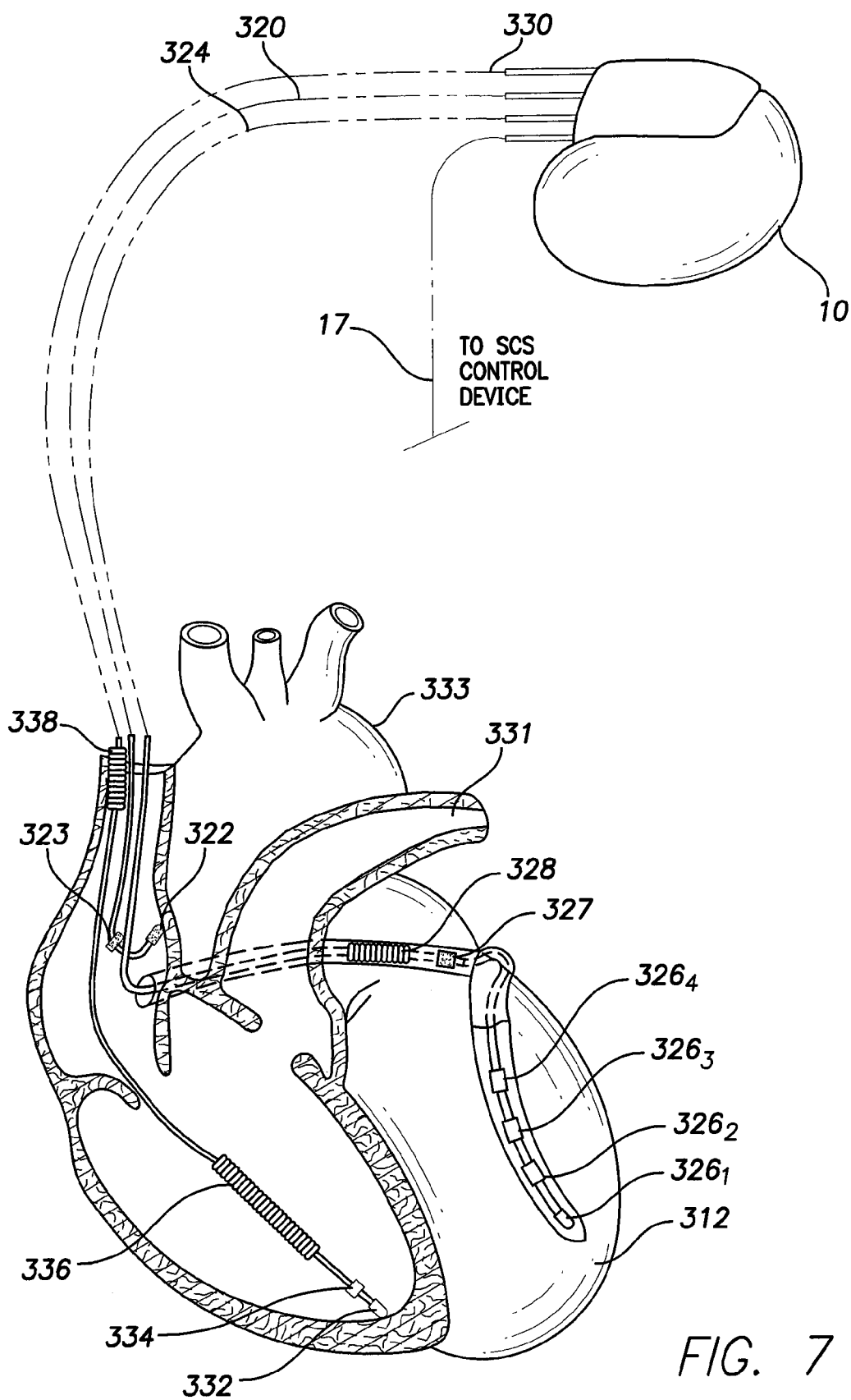
FIG. 7 is a simplified, partly cutaway view of the heart of a patient, illustrating the exemplary CRMD of FIG. 1, along with a set of leads implanted in the heart of the patient.

FIG. 1 illustrates an implantable medical system 8 having a CRMD 10 equipped to control neurostimulation based on regional cardiac performance, particularly SCS. The assessment of regional cardiac performance is performed based on IEGM signals and electrical impedance measurements obtained via a set of leads 12. Three exemplary leads—RA, RV and LV/CS—are shown in FIG. 1 (in stylized form) for sensing IEGM signals and measuring impedance. A more complete set of leads is illustrated in FIG. 7, described below. In the example of FIG. 1, the LV/CS lead is a quadpole lead as indicated by a set of four electrodes 14, which facilitate obtaining cardiogenic impedance measurements along a variety of impedance vectors to assess regional cardiac performance. While assessing regional cardiac performance, the CRMD controls an implantable SCS device 16 (or other suitable implantable neurostimulation device) via an interconnection lead 17 to deliver neurostimulation using one or more SCS electrodes/leads such as paddle lead 18. In this example, SCS electrode/lead 18 is implanted along the spine for delivering neurostimulation to nerves in or near the spine but might be implanted elsewhere in other implementations.

The CRMD controls implantable SCS device 16 to deliver neurostimulation via lead 18 using a variety of combinations of neurostimulation control parameters (such as pulse frequency, amplitude, duration, etc.) while regional cardiac performance is concurrently assessed based on cardiogenic impedance measurements obtained along various vectors through or near the heart. Data relating regional cardiac performance to various combinations of neuromodulation control parameters is then stored and analyzed by the CRMD to identify a combination of neuromodulation control parameters that serve to improve or maximize any beneficial effect on cardiac performance by the neurostimulation. As will be explained, this data may be collected and analyzed for various postures and diurnal states so that neurostimulation can be tailored based on posture and/or time of day.

Diagnostic data may be transmitted to an external CRMD device programmer, personal advisory module (PAM), bedside monitor, external SCS controller or other external system 20. Additionally, warning signals pertaining to any significant deterioration is cardiac performance can be transmitted to the external system to alert the patient or caregivers. The external system can forward warning signals or other suitable information via a centralized processing system 22 to the patient's primary care physician or others. The centralized system may include such systems as the HouseCall™ remote monitoring system or the Merlin@home/Merlin.Net systems of St. Jude Medical. Warnings pertinent to a deterioration in cardiac performance may also be generated using an internal warning device provided within the CRMD. The internal warning device can be a vibrating device or a "tickle" voltage device that, in either case, provides perceptible stimulation to the patient to alert the patient. If equipped with an SCS controller, the external system 20 may allow the patient to transmit control signals directly to the implanted SCS device to override neuromodulation control parameters generated by the CRMD, if needed to mitigate pain for which the SCS device might have been initially implanted, such as lower back pain.

Additionally, the CRMD performs a wide variety of pacing and/or defibrillation functions, such as delivering routine pacing for bradycardia or generating and delivering shocks in response to ventricular fibrillation (VF.) Also, in some examples, the device is equipped to deliver CRT. Briefly, CRT seeks to normalize asynchronous cardiac electrical activation and resultant asynchronous contractions associated with congestive heart failure (CHF) by delivering synchronized pacing stimulus to both ventricles. The stimulus is synchronized so as to improve overall cardiac function. This may have the additional beneficial effect of reducing the susceptibility to life-threatening tachyarrhythmias.

Figure 2:
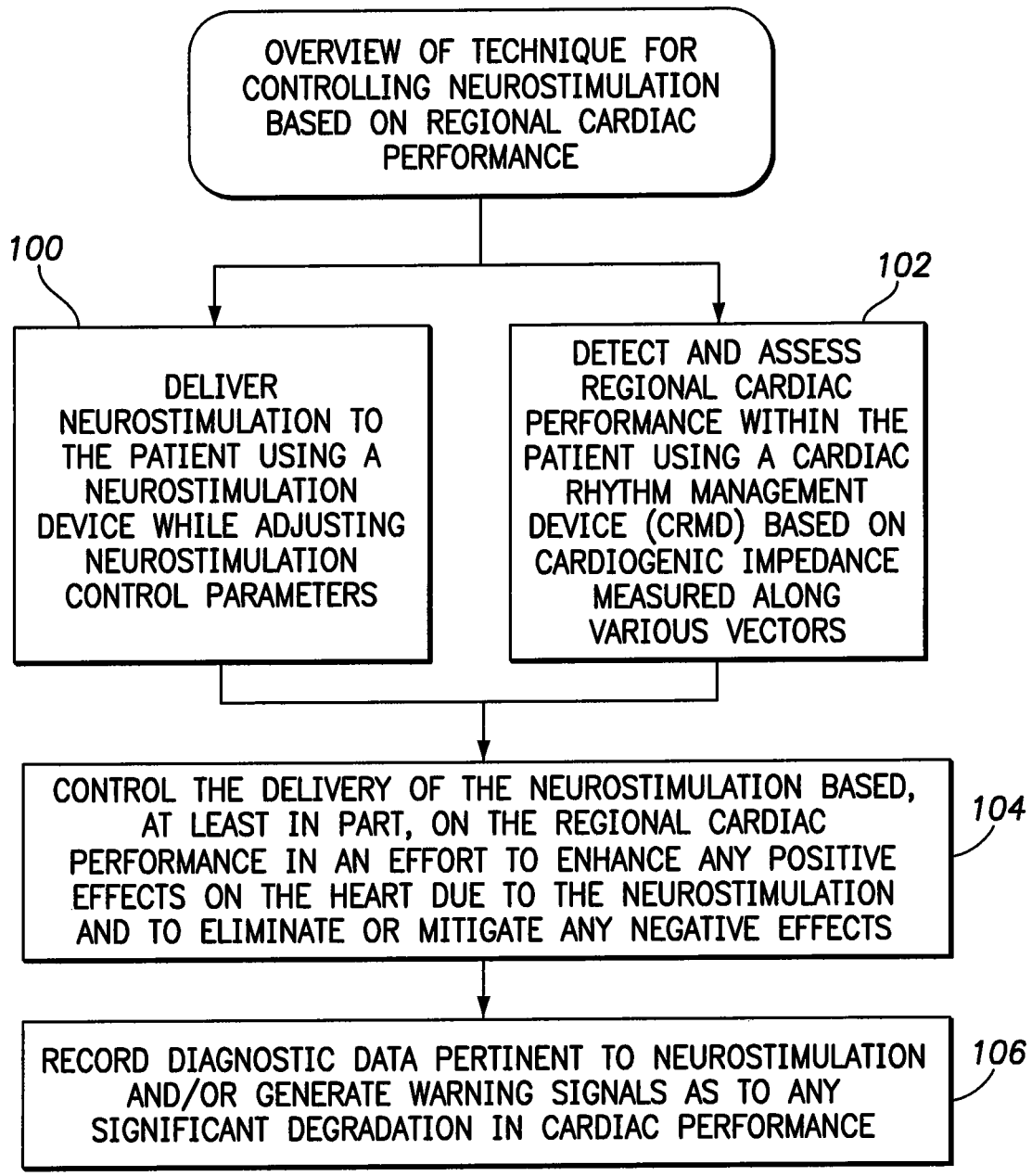
FIG. 2 is an overview of the method for controlling neurostimulation based on regional cardiac performance performed by the system of FIG. 1.

FIG. 2 broadly summarizes the neurostimulation control procedures implement by the CRMD of FIG. 1 or other suitable equipped implantable medical systems. Initially, at step 100, the system delivers neurostimulation to the patient using the neurostimulation device while adjusting neurostimulation parameters (aka neuromodulation parameters) through ranges of programmable values. Concurrently, at step 102, the system assesses or evaluates regional cardiac performance within the patient using the CRMD, based on cardiogenic impedance measured along various vectors. At step 104, the system controls the delivery of additional neurostimulation based, at least in part, on regional cardiac performance in an effort to enhance any positive effects on the heart due to neurostimulation and to eliminate or mitigate any negative effects. At step 106, the device records diagnostic data pertinent to neurostimulation and/or generates warning signals, if warranted.

Thus, FIGS. 1 and 2 provide a broad overview of exemplary systems and methods for controlling neurostimulation based on regional cardiac performance. Embodiments may be implemented that do not necessarily perform all of the described functions. For example, embodiments may be implemented that provide, for example, for controlling neurostimulation but which do not automatically generate and transmit warnings pertaining to changes in cardiac performance. Bedside monitors or PAMs are not necessarily used. Some implementations may employ some form of external device for generating warning signals but no internal warning device. Other embodiments might include additional implanted devices or components, such as physiological sensors implanted within the heart. These are just a few exemplary embodiments. No attempt is made herein to describe all possible combinations of components that might be provided in accordance with the general principles of the invention.

Also, note that, the particular shapes, sizes and locations of the implanted components shown in FIG. 1 are merely illustrative and may not necessarily correspond to actual implant locations. Preferred implant locations for the leads are more precisely illustrated in FIG. 7. In some cases, rather than interconnecting components via implantable leads, suitable wireless communication systems and channels might be employed. As one example, the neuromodulation control parameters generated by the CRMD might be transmitted to the external system 20, which then relays the signals to implanted neurostimulation device 16 so that interconnection lead 17 is not required.

Exemplary Cardiac Performance-Based SCS Control Techniques

FIGS. 3-1, 3-2 and 4 illustrate an exemplary technique for controlling neurostimulation using a CRMD based on regional cardiac performance wherein the neurostimulation is SCS. Initially, at step 200 of FIG. 3-1, the CRMD detects diurnal status (e.g. time of day, diurnal rate, diurnal variation or other diurnal parameters) and the current patient posture (e.g. sitting, standing, lying down, left sided lying, right sided lying, etc.) Techniques for detecting patient posture are described in, for example, U.S. Pat. No. 7,149,584 to Koh et al., entitled "System and Method for Determining Patient Posture based on 3-D Trajectory using an Implantable Medical Device." Diurnal parameters are discussed, for example, in U.S. Pat. No. 7,711,415 to Farazi et al., entitled "Implantable Devices, and Methods for use therewith, for Monitoring Sympathetic and Parasympathetic Influences on the Heart" and in U.S. Pat. No. 6,058,328 to Levine et al., entitled "Implantable Stimulation Device having Means for Operating in a Preemptive Pacing Mode to Prevent Tachyarrhythmias and Method thereof."

At step 202, the CRMD controls the implanted SCS device to deliver SCS while adjusting neuromodulation parameters through ranges of programmable values such as: pulse amplitude (0.1-5.5 mA); pulse frequency (2-500 Hz); pulse width (1-1000 μsec); and SCS duration (5 seconds to 15 minutes), while cycling through combinations of electrode pairs to control the depth of the SCS electric field, preferably within guarded cathode configurations. The time duration for stimulation can impact the desired effects to be mapped: 5 sec for short term effects since neurotransmitter release occurs within seconds. Longer term effects (e.g. cardioprotective effects) can be monitored by giving 15 minutes of SCS. See, for example, Ardell et al., "Dorsal spinal cord stimulation obtunds the capacity of intrathoracic extracardiac neurons to transduce myocardial ischemia" Am. J. Physiol., Regul Integr Comp Physiol 2009; 297:R470-R477. (Note: A guarded cathode is a configuration in which two contacts—programmed as anodes—bracket another contact, which is programmed as a cathode. The boundary created by the anodes for the depolarizing effect of the cathode helps to create an area of paresthesia. In general, patients seem to prefer a guarded cathode array. In this regard, in the guarded cathode configuration, a cathode is bordered by anodes. Computer modeling has shown that a guarded cathode on the midline can provide maximal recruitment of the dorsal column and clinical studies have observed a patient preference for this configuration.)

Each unique set of SCS control parameters used in step 202 is stored as a different "parameter configuration" entry in a table within the CRMD (i.e. within a corresponding data array portion of internal device memory), as shown by way of table 203 in FIG. 4, which includes a set of separate entries 205. For example, the first entry $205_1$ in the table may specify a pulse amplitude of 0.1 mA, a pulse frequency of 2 Hz, a pulse width 1 μsec, etc.; whereas the second entry may specify a pulse amplitude of 1.0 mA, a pulse frequency of 2 Hz, a pulse width 1 μsec, etc.; with a separate entry $205_n$ stored for each unique set of control parameters that is tested by the CRMD, where N is the total number of unique sets of parameters that are tested.

Figures 1, 3:
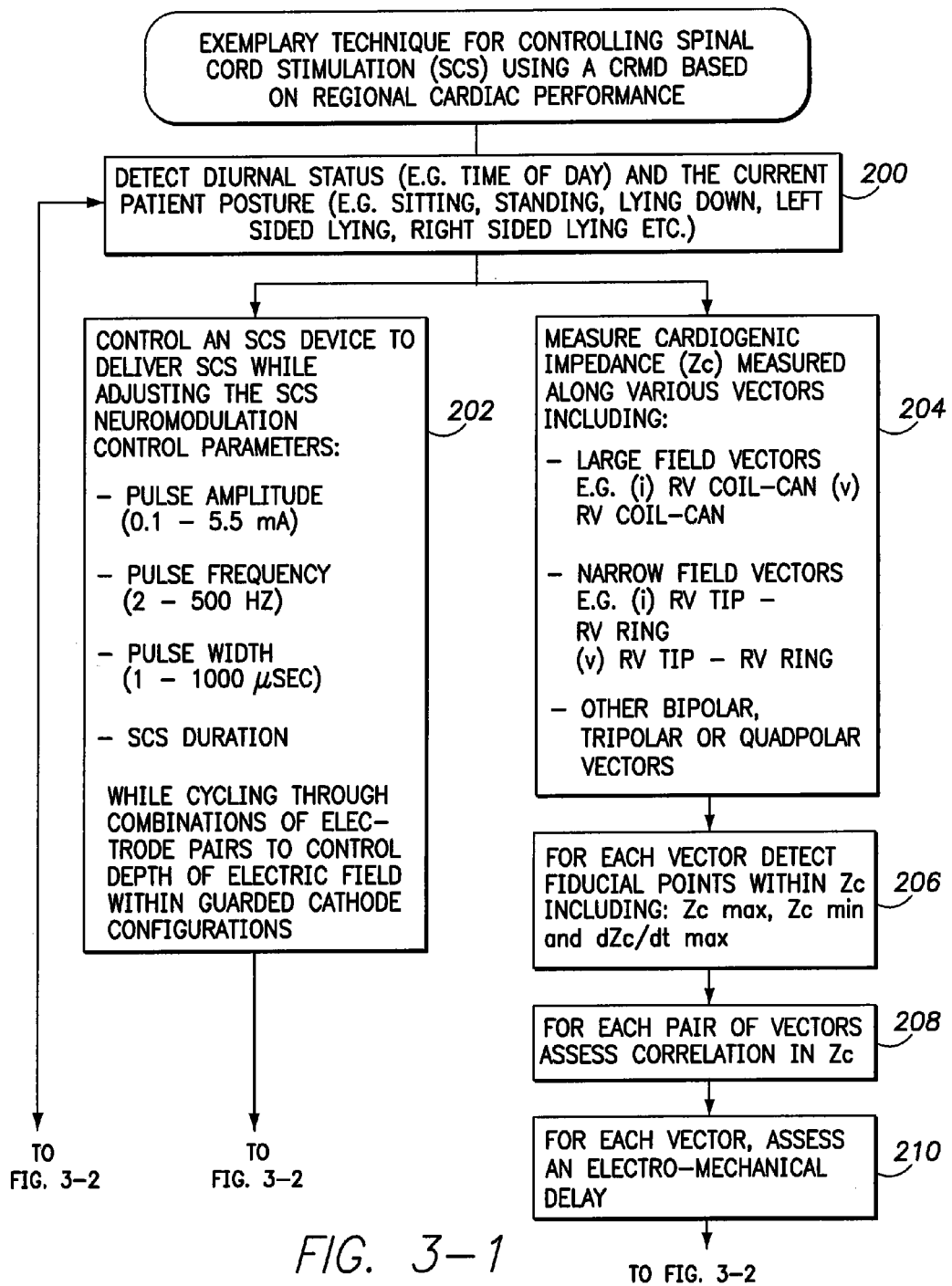
Figures 2, 3:
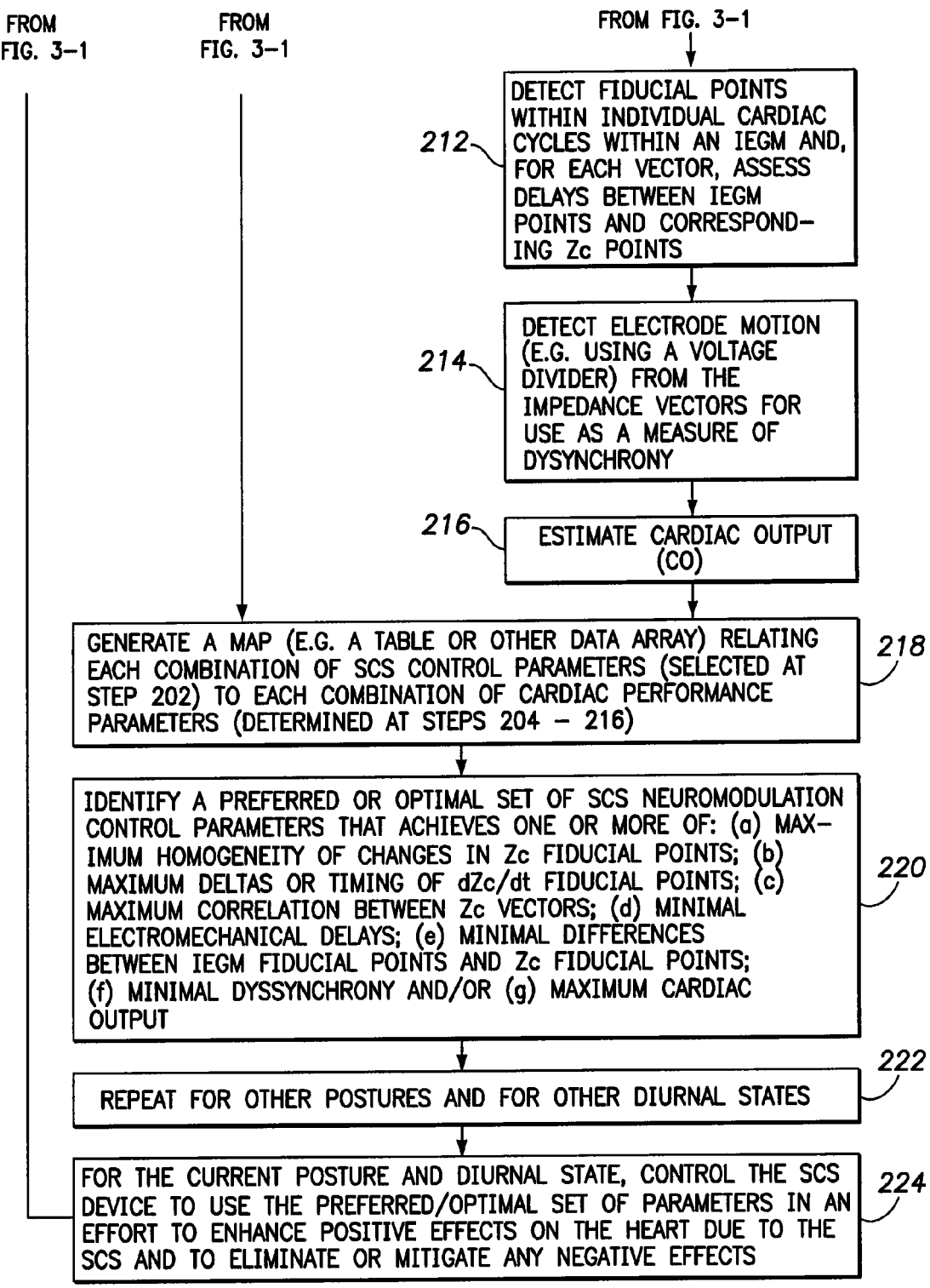

Concurrently, for each unique set of SCS parameters that is tested, the CRMD performs steps 204-216 of FIGS. 3-1 and 3-2 to assess the regional cardiac performance associated with the given set of SCS parameters along various impedance vectors. Depending upon the implementation, the CRMD may deliver SCS with a particular set of neuromodulation parameters for some predetermined minimum amount of time before cardiac performance is assessed to allow the heart to respond to any parasympathetic or sympathetic changes in the patient brought on by the SCS (or generally associated therewith.) To assess cardiac performance, beginning at step 204, the CRMD measures cardiogenic impedance (Zc) along various selected vectors including: large field vectors (e.g. (i) RV coil-can with (v) RV coil-can); narrow field vectors (e.g. (i) RV tip—RV ring with (v) RV tip—RV ring); or other bipolar, tripolar or quadpolar vectors. In the foregoing, the "i" refers to the vector for injecting current; the "v" refers to the vector for measuring the resulting voltage from which impedance is derived. Each selected impedance vector may be denoted numerically, such as Vector #1, Vector #2, etc. As noted above, related electrical parameters might be detected and/or exploited besides impedance, such as admittance, conductance or immittance. Those skilled in the art can convert among these related parameters as needed. A particularly effective tri-phasic impedance detection pulse for use in detecting impedance is described in U.S. patent application Ser. No. 11/558,194 of Panescu et al., filed Nov. 9, 2006, entitled "Closed-Loop Adaptive Adjustment of Pacing Therapy based on Cardiogenic Impedance Signals Detected by an Implantable Medical Device." See, also, techniques described in U.S. patent application Ser. No. 13/007,424 of Gutfinger et al., filed Jan. 14, 2011, entitled "Systems and Methods for Exploiting Near-Field Impedance and Admittance for use with Implantable Medical Devices" and U.S. patent application Ser. No. 12/853,130 of Gutfinger et al., filed Aug. 9, 2010, entitled "Near Field-Based Systems and Methods for Assessing Impedance and Admittance for use with an Implantable Medical Device."

Figure 5:
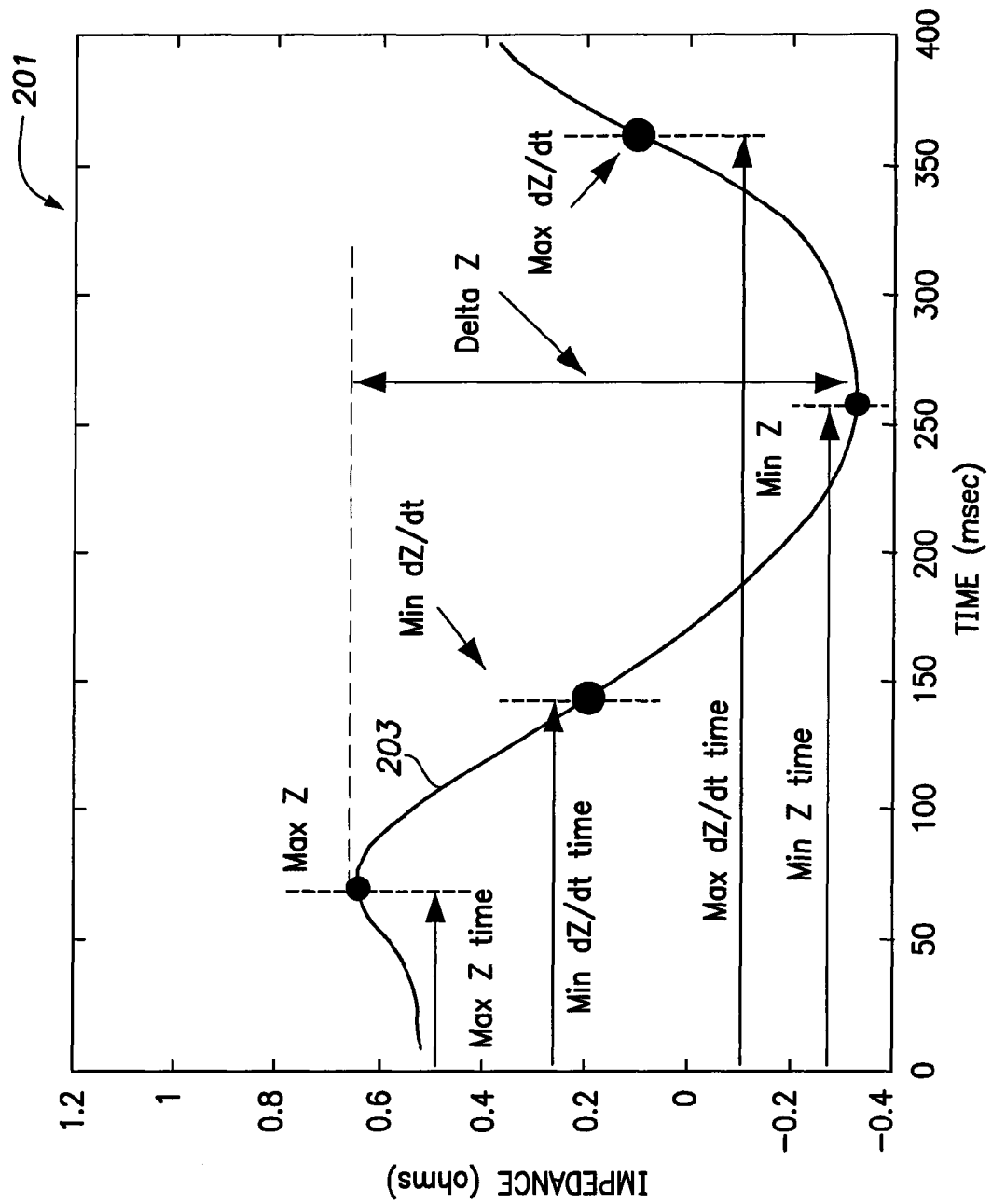
FIG. 5 is a graph illustrating impedance fiducial points that may be exploited by the method of FIGS. 3-1 and 3-2.

At step 206, for each unique impedance vector, the CRMD detects selected fiducial points within Zc including: Zc max, Zc min, dZc/dt max and dZc/dt min (i.e. the maximum negative value of dZc/dt.) FIG. 5 illustrates these and other fiducial points with reference to graph 201, which shows an impedance trace 203 and various fiducial points with timings and deltas therebetween. Referring again to FIG. 4, at step 208, for each pair of unique impedance vectors, the CRMD assesses the degree of correlation in Zc between the vectors. Otherwise conventional techniques may be used to quantify or assess the degree of correlation. Correlation techniques are discussed, for example, in U.S. Published Application 2010/0114228 of Bharmi et al., entitled "System and Method for Accurately Detecting Cardiac Events using Retrospective Correlation." At step 210, for each impedance vector, the CRMD assesses or detects an electromechanical delay such as by assessing a delay between features of an IEGM signal and changes in cardiac pressure measured using a physiological sensor, as discussed in U.S. Pat. No. 8,016,764 to Shelchuk, entitled "Systems and Methods for Evaluating Ventricular Dyssynchrony using Atrial and Ventricular Pressure Measurements obtained by an Implantable Medical Device." At step 212, the CRMD detects fiducial points within an IEGM (such as the peak of the QRS complex within a ventricular IEGM or the peak of the P-wave within an atrial IEGM) and, for each unique impedance vector, the device assesses delays between IEGM points and corresponding Zc points. The time delay between a fiducial point in the IEGM and a corresponding fiducial point in the impedance signal represents another measure of electromechanical delay, which may be exploited in addition to (or as an alternative to) the electromechanical delay obtained at step 210. At step 214, the CRMD detects electrode motion (e.g. using a voltage divider) from the impedance vectors for use as a measure of dyssynchrony. The use of electrode motion to assess dyssynchrony is discussed, for example, in U.S. Pat. No. 8,019,409 Rosenberg et al., entitled "Cardiac Resynchronization Therapy Optimization using Electromechanical Delay from Realtime Electrode Motion Tracking."

At step 216, the CRMD detects or estimates CO. If so equipped, a different CO value may be estimated from stroke volume (SV) determined from impedance (where CO=SV*HR) for each of the selected impedance vectors (or at least from some of the impedance vectors, such as one passing through the RV and one passing through the LV.) In this regard, various groups have studied Stroke Volume estimation using impedance. See, for example, Zima et al., "Determination of left ventricular volume changes by intracardiac conductance using a biventricular electrode configuration" Europace. 2006; 8:537-544; Stahl et al., "Assessing Acute Ventricular Volume Changes by Intracardiac Impedance in a Chronic Heart Failure Animal Model" PACE 2009; 32:1395-1401; Bocchiardo et al, "Intracardiac impedance monitors stroke volume in resynchronization therapy patients" Europace 2010; 12:702-707 showing that conductance of the ventricle increases during diastole due to ventricular filling and increased distance between electrodes. The conductance decreases during systole and reaches its maximum at the end of ejection phase. The difference between this end diastolic volume and end systolic volume is a good measure of stroke volume. An unpublished internal study (by the assignee company of the present invention) has shown that SV can be determined (as a hemodynamic parameter) from different impedance vectors. Cardiogenic impedance can be recorded from multiple sites e.g. current from RA Tip-Case voltage measured from RA ring-Case, current from SVC coil-Case while measuring voltage from SVC coil-Case (giving large field impedance measures) or injecting current from RV tip-Case and measuring voltage from RV ring-case (giving specific local cardiac field measures). Depending on the vector used, the regional blood flow can be measured.

Exemplary parameters for estimating SV (and hence CO) from impendence include max dZ/dt, Z area–Max to Min, Rectified Z area and related parameters such as Zarea5 and PSD1 where Zarea5 is an integral of rectified impedance over a range of, for example, 321:400 ms and PSD1 is a power spectral density over a frequency range of, for example, 1.5-3.5 Hz. See, FIG. 6, which provides a graph 209 showing SV 211 (illustrated via unconnected dots) and estimated SV 213 (illustrated via connected dots) wherein SV is estimated based on the aforementioned impedance parameters for a healthy canine test subject. In this example, various interventions were applied to the test subject to modify SV and, as can be seen, the estimated SV 219 tracked the actual SV fairly well. In this example, the interventions included LV, AVD 120, CNTL3, AVD 100, AVD 25 and CNTL5 wherein exemplary details are as follows.

Figure 6:
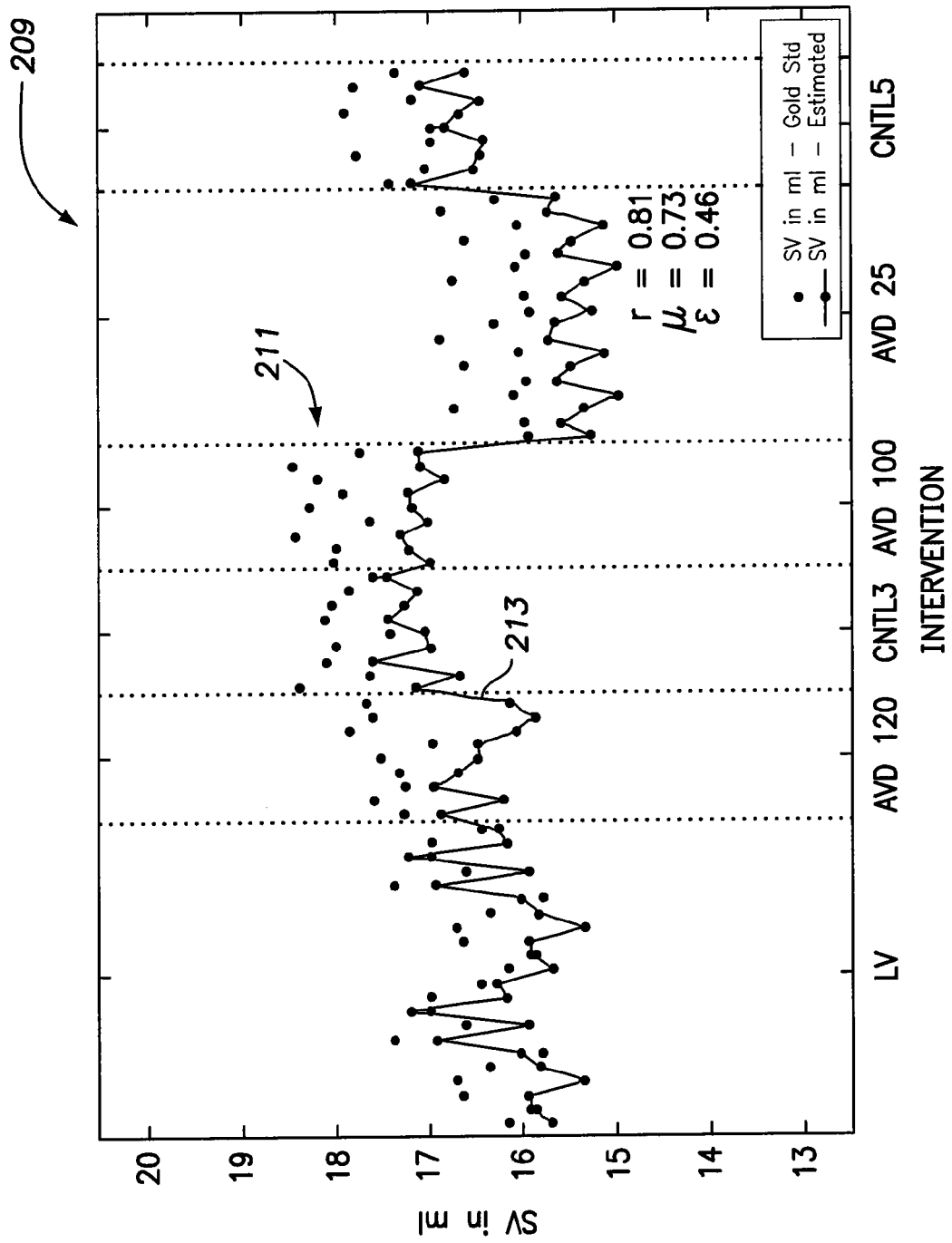
FIG. 6 is a graph illustrating stroke volume estimated using impedance-based techniques that may be exploited by the method of FIGS. 3-1 and 3-2 to assess cardiac output.

LV: Pacing in LV VOO mode at 150 bpm
    AVD 120: Pacing in BiV simultaneous mode at 150 bpm with an AV delay of 120 ms
    CNTL3: Pacing in BiV simultaneous mode at 150 bpm with an AV delay of 80 ms
    AVD 100: Pacing in BiV simultaneous mode at 150 bpm with an AV delay of 100 ms
    AVD 25: Pacing in BiV simultaneous mode at 150 bpm with an AV delay of 25 ms
    CNTL5: Pacing in BiV simultaneous mode at 150 bpm with an AV delay of 80 ms It should be understood that the data in FIG. 6 represents just one specific example showing a model estimating SV using impedance features and setting forth some possible performance metrics of the estimation (such as an r value of 0.81, a μ of 0.73 and an ϵ of 0.56.) It is provided for illustrative purposes.

See, also, Stahl et al., "Assessing acute ventricular volume changes by intracardiac impedance in a chronic heart failure animal model." Pacing Clin Electrophysiol. 2009 November; 32(11):1395-401. Epub 2009 Sep. 19, and Bocchiardo et al., "Resynchronization therapy optimization by intracardiac impedance" Europace. 2010 November; 12(11):1589-95. Epub 2010 Jul. 28. In other implementations, a single CO value is assessed for the patient. Techniques for detecting CO from impedance are discussed, for example, in U.S. Pat. No. 6,134,472 to Strandberg et al., entitled "Heart Stimulation Device." See, also, U.S. Pat. No. 7,925,347 to Bornzin, entitled "Assessment of Cardiac Output by Implantable Medical Device"; U.S. Pat. No. 7,632,235 to Karicherla et al., entitled "System and Method for Measuring Cardiac Output via Thermal Dilution using an Implantable Medical Device with an External Ultrasound Power Delivery System"; U.S. Pat. No. 7,139,609 to Min et al., entitled "System and Method for Monitoring Cardiac Function Via Cardiac Sounds using an Implantable Cardiac Stimulation Device"; U.S. Pat. No. 6,314,323 to Ekwall, entitled "Heart Stimulator Determining Cardiac Output, by Measuring the Systolic Pressure, for Controlling the Stimulation"; and U.S. Published Application 2009/0187087 of Turcott, entitled "Analysis of Metabolic Gases by an Implantable Cardiac Device for the Assessment of Cardiac Output."

At step 218, the CRMD generates a map (e.g. a table) relating each combination of SCS neuromodulation control parameters (selected at step 202) to each combination of cardiac performance parameters (obtained during steps 204-216). That is, for each unique impedance vector selected in step 204 and for each unique SCS parameter configuration specified in step 202, the corresponding set of cardiac performance parameters measure by the CRMD in steps 206-216 is stored as a different "regional cardiac performance" entry in a table within the memory of the CRMD, as shown by way of tables $217_1, 217_2, \ldots, 217_N$ in FIG. 4. For example, the first table 217 may correspond to Vector #1 (e.g. (i) RV coil-can with (v) RV coil-can). The second table $217_2$ may correspond to Vector #2 (e.g. (i) RV tip—RV ring with (v) RV tip—RV ring.) Each line entry in a particular table, such as entry $219_1$ of table $217_1$, corresponds to the set of SCS parameters used while that particular set of cardiac performance parameters was measured using that particular vector. For example, line $219_1$ of table $217_1$ represents the cardiac performance parameters measured using impedance Vector #1 while the SCS parameters of entry $205_1$ were being used to control SCS. Line $219_N$ of table $217_1$ represents the cardiac performance parameters measured using impedance Vector #1 while the SCS parameters of entry $205_N$ were being used. As another example, line $221_1$ of table $217_2$ represents the cardiac performance parameters measured using impedance Vector #2 while the SCS parameters of entry $205_1$ were being used. Line $221_N$ of table $217_2$ represents the cardiac performance parameters measured using impedance Vector #2 while the SCS parameters of entry $205_N$ were being used.

In this manner, a different table is stored for each impedance vector with each table mapping a set of regional cardiac performance parameters to corresponding SCS parameter configurations (although a single multi-dimensional data array could instead be used.) Hence, the entire data set serves to map all tested SCS parameter configurations to all of the resulting sets of regional cardiac performance parameters, and vice versa, allowing the device to identify a particular set of SCS control parameters that achieves improved cardiac performance, either globally (as represented by all of the impedance vector tables) or locally (as represented by a selected one of the impedance vector tables that might indicate cardiac performance within a particular chamber of the heart such as the LV.)

Accordingly, at step 220, the CRMD then identifies a preferred or optimal set of SCS neuromodulation control parameters that achieves one or more of: (a) maximum homogeneity of changes in Zc fiducial points; (b) maximum deltas or timings of dZc/dt fiducial points (see, again, FIG. 5); (c) maximum correlation between Zc vectors; (d) minimal electromechanical delays; (e) minimal differences between IEGM fiducial points and Zc fiducial points; (f) minimal dyssynchrony and/or (g) maximum cardiac output, or some combination thereof. Insofar as (a) and (b) are concerned, different impedance vectors reflect regional or large field cardiac/systemic responses. Hence, a best set of SCS parameters would be one wherein all or most fiducial points (such as those discussed above in connection with FIG. 5) are homogenous or at least trending in the same direction. In this regard, a set of SCS parameters that causes the maximal effect is preferable to another set of parameters, e.g., if a given set of SCS parameters causes the Delta Z (positive peak to negative peak Cardiogenic impedance signal) to be high in most vectors, i.e. indicating a higher cardiac output status, then that set of SCS parameters would be preferred.

In one example, a metric value representing a combination of any or all of these parameters may be assessed by the device to facilitate identifying a preferred or optimal set of SCS control parameters. Techniques for generating a combined metric based on various parameters for evaluation are discussed in: U.S. Pat. No. 7,207,947 to Koh et al., entitled "System and Method for Detecting Circadian States Using an Implantable Medical Device." In other examples, the collected data is transmitted to a clinician who chooses the set of SCS parameters to be used based on an examination of the data. Note that, the cardiac performance data collected at steps 204-216 and analyzed at steps 218-220 corresponds to the particular posture and diurnal state in which the data was collected. At step 222, if so programmed, the CRMD may then repeat the entire procedure to generate corresponding tables for mapping cardiac performance to SCS control parameters for other postures and/or other diurnal states (e.g. day, night, etc.) Hence, an entirely different set of tables would be generated and stored in the CRMD for each unique posture and/or diurnal state (or a suitable multidimensional data array would be used.)

At step 224, for the current posture and diurnal state, the CRMD controls the SCS device to use the preferred/optimal set of parameters identified at step 220 in an effort to enhance positive effects on the heart due to (or associated with) the SCS and eliminate or mitigate any negative effects. It should be understood that any "optimal" neuromodulation control parameters obtained using techniques described herein are not necessarily absolutely optimal in a given quantifiable or mathematical sense. What constitutes "optimal" depends on the criteria used for judging the resulting performance, which can be subjective in the minds of patients and clinicians. The neuromodulation control parameters identified or selected using the techniques described herein represent, at least, a "preferred" set of neuromodulation control parameters. Clinicians (or in some case patients) may choose to adjust or alter the neuromodulation control parameters at their discretion using suitable external control devices. Also, although specifically shown in FIGS. 3-1 and 3-2, the CRMD may record suitable diagnostic information, such as the lists of the neuromodulation parameters selected, as well as warnings pertaining to any deteriorating cardiac conditions, if such is indicated by the regional cardiac performance parameters.

The techniques of FIGS. 3-1, 3-2 and 4 may be used, where appropriate, in conjunction with other techniques. See, for example, the neurostimulation techniques described in U.S. patent application Ser. No. 13/563,417, filed Jul. 31, 2012, of Min et al., entitled "Systems and Methods for Controlling Neurostimulation of Acupuncture Sites using an Implantable Cardiac Rhythm Management Device". Insofar as assessing and improving cardiac performance is concerned, see also, techniques discussed in U.S. Published Application 2010/0152801 to Koh et al., entitled "Cardiac Resynchronization Therapy Optimization using Vector Measurements Obtained from Realtime Electrode Position Tracking"; U.S. Pat. No. 5,891,176 to Bornzin, entitled "System and Method for Providing Hemodynamically Optimal Pacing"; U.S. Pat. No. 5,549,650 to Bornzin et al., entitled "System and Method for Providing Hemodynamically Optimal Pacing Therapy"; U.S. Pat. No. 7,627,374 Farazi et al., entitled "System and Method for Evaluating and Optimizing the Contribution of Particular Heart Chambers to the Overall Efficacy of Cardiac Pacing Therapy"; and U.S. Pat. No. 7,826,899 to Ryu et al., entitled "Neurostimulation and Neurosensing Techniques to Optimize Atrial Anti-Tachycardia Pacing for Termination of Atrial Tachyarrhythmias." See, also, U.S. Published Application 2010/0331921 of Bornzin et al., entitled "Neurostimulation Device and Methods for Controlling Same"; U.S. Published Application 2010/0057158 of Rodriguez et al., entitled "Neurostimulation Based on Glycemic Condition"; U.S. Pat. No. 7,164,944 to Kroll et al., entitled "Analgesic Therapy for ICD Patients." SCS is also discussed, e.g., in U.S. Pat. No. 7,099,718 to Thacker, et al. Techniques for stimulating sympathetic nerves are discussed in U.S. Pat. No. 6,937,896 to Kroll, entitled "Sympathetic Nerve Stimulator and/or Pacemaker."

Although the foregoing examples primarily pertain to SCS, other forms of neurostimulation may be applied and controlled. Insofar as the neurostimulation sites are concerned, the sites for implantation of the neurostimulation electrodes may be selected while taking dermatomes into consideration. Briefly, a dermatome refers to an area of skin primarily supplied by a single spinal nerve. Accordingly, neurostimulation device(s) may be implanted, where feasible, near the nerves leading to selected dermatomes. For the sake of completeness, the spinal nerves and points characteristically belonging to the dermatome of each nerve are listed herein and include: C2—lateral to the occipital protuberance at the base of the skull; C3—in the supraclavicular fossa, at the midclavicular line; C4—over the acromioclavicular joint; C5—on the lateral (radial) side of the antecubital fossa; C6—on the dorsal surface of the proximal phalanx of the thumb; C7—on the dorsal surface of the proximal phalanx of the middle finger; C8—on the dorsal surface of the proximal phalanx of the little finger; T1—on the medial (ulnar) side of the antecubital fossa, just proximally to the medial epicondyle of the humerus; T2—at the apex of the axilla; T3—intersection of the midclavicular line and the third intercostal space; T4—intersection of the midclavicular line and the fourth intercostal space; T5—intersection of the midclavicular line and the fifth intercostal space; T6—intersection of the midclavicular line and the horizontal level of the xiphoid process; T7—intersection of the midclavicular line and the horizontal level at one quarter the distance between the level of the xiphoid process and the level of the umbilicus; T8—intersection of the midclavicular line and the horizontal level at one half the distance between the level of the xiphoid process and the level of the umbilicus; T9—intersection of the midclavicular line and the horizontal level at three-quarters of the distance between the level of the xiphoid process and the level of the umbilicus; T10—intersection of the midclavicular line, at the horizontal level of the umbilicus; T11—intersection of the midclavicular line, at the horizontal level midway; T12—intersection of the midclavicular line and the midpoint of the inguinal ligament; L1—midway between the key sensory points for T12 and L2; L2—on the anterior medial thigh, at the midpoint of a line connecting the midpoint of the inguinal ligament and the medial epicondyle of the femur; L3—at the medial epicondyle of the femur; L4—over the medial malleolus; L5—on the dorsum of the foot at the third metatarsophalangeal joint; S1—on the lateral aspect of the calcaneus; S2—at the midpoint of the popliteal fossa; S3—over the tuberosity of the ischium or infragluteal fold; S4 and S5—in the perianal area, less than one cm lateral to the mucocutaneous zone.

The above-described techniques can be implemented with a variety of implantable medical devices. For the sake of completeness, a CRMD implementation will now be described in detail.

Exemplary CRMD

Figure 8:
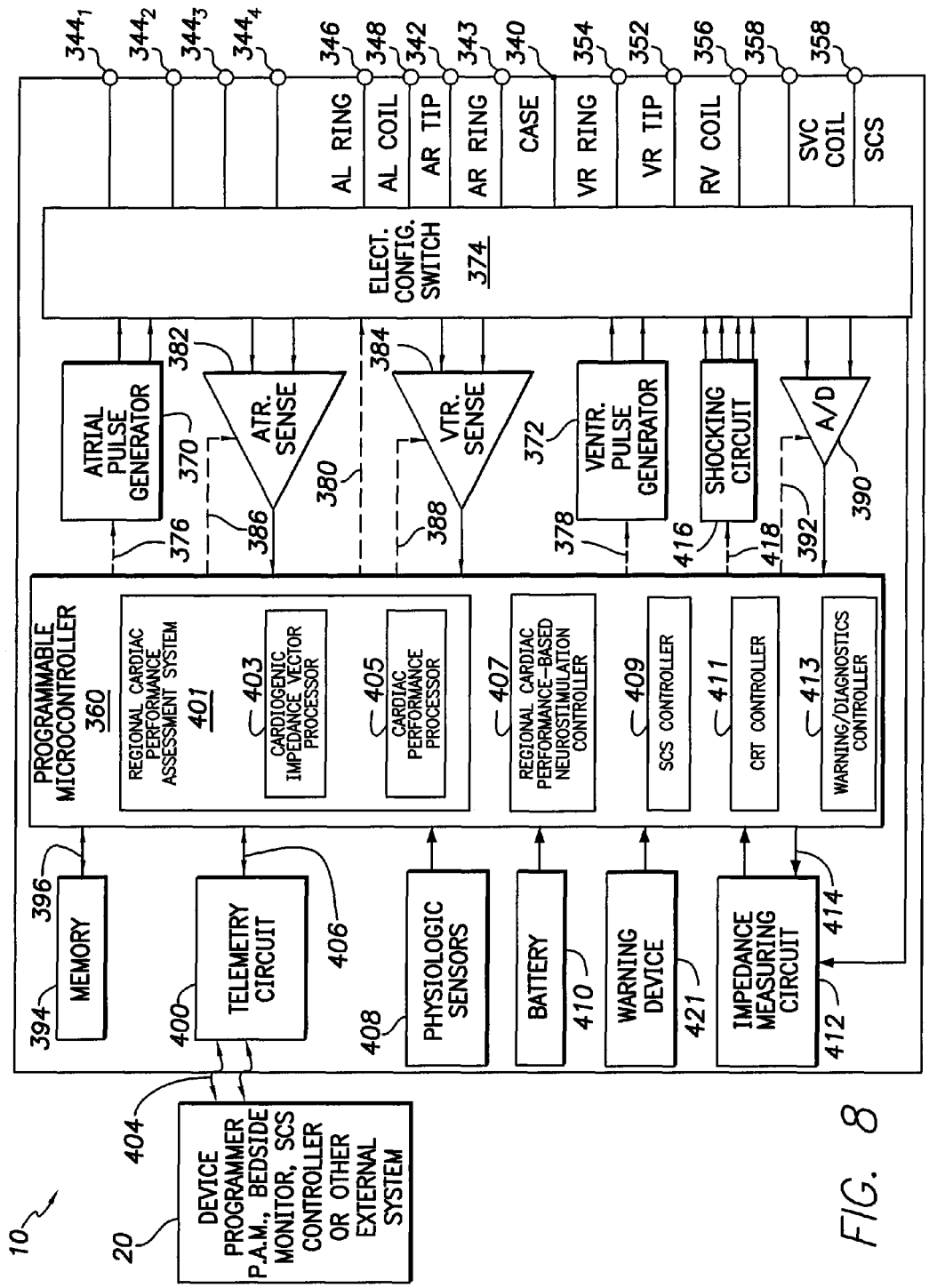
FIG. 8 is a functional block diagram of the CRMD of FIG. 7, illustrating basic device circuit elements that provide cardioversion, defibrillation and/or pacing stimulation in four chambers of the heart, and particularly illustrating components for controlling neurostimulation.

With reference to FIGS. 7 and 8, a description of an exemplary CRMD will now be provided. FIG. 7 provides a simplified block diagram of the device, which is a dual-chamber stimulation device capable of treating both fast and slow arrhythmias with stimulation therapy, including cardioversion, defibrillation, and pacing stimulation, and also capable of controlling neurostimulation as discussed above. To provide right atrial chamber pacing stimulation and sensing, device 10 is shown in electrical communication with a heart 312 by way of a right atrial lead 320 having an atrial tip electrode 322 and an atrial ring electrode 323 implanted in the atrial appendage. Device 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, device 10 is coupled to a multi-pole LV lead 324 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 324 is designed to receive atrial and ventricular cardiac signals and to deliver left ventricular pacing therapy using a set of four left ventricular electrodes $326_1$, $326_2$, $326_3$, and $326_4$ (thereby providing a quad-pole lead), left atrial pacing therapy using at least a left atrial ring electrode 327, and shocking therapy using at least a left atrial coil electrode 328 implanted on or near the left atrium. In other examples, more or fewer LV electrodes are provided. Although only three leads are shown in FIG. 7, it should also be understood that additional leads (with one or more pacing, sensing and/or shocking electrodes) might be used and/or additional electrodes might be provided on the leads already shown.

Additionally, a neurostimulation control lead 17 is provided for connecting the CRMD to one or more neurostimulation control devices such as device 16 of FIG. 1 (or directly to neurostimulation electrodes such as paddle 18 of FIG. 1 if the CRMD is equipped to directly control neurostimulation.) Additional leads may be required to control neurostimulation depending upon the number of neurostimulation devices and their locations.

A simplified block diagram of internal components of device 10 is shown in FIG. 8. While a particular device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 340 for device 10, shown schematically in FIG. 8, is often referred to as the "can," "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344$_1$-344$_4$, 346, 348, 352, 354, 356, 358 and 359 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes a left ventricular tip terminal (VL$_1$ TIP) 344$_1$ and additional LV electrode terminals 344$_2$-344$_4$ for the other LV electrodes of the quadra-pole LV lead. A terminal 359 is shown for connection to neurostimulation control lead 17. Depending upon the particular neurostimulation system, additional terminals may be needed.

The connector also includes a left atrial ring terminal ($A_L$ RING) 346 and a left atrial shocking terminal ($A_L$ COIL) 348, which are adapted for connection to the left atrial ring electrode 327 and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($V_R$ COIL) 356, and an SVC shocking terminal (SVC COIL) 358, which are adapted for connection to the right ventricular tip electrode 332, right ventricular ring electrode 334, the $V_R$ coil electrode 336, and the SVC coil electrode 338, respectively.

At the core of CRMD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 8, an atrial pulse generator 370 and a ventricular pulse generator 372 generate pacing stimulation pulses for delivery by the right atrial lead 320, the right ventricular lead 330, and/or the CS lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, CS lead 324, and the right ventricular lead 330, through the switch 374 for detecting the presence of cardiac activity in each of the four chambers of the heart. Accordingly, the atrial and ventricular sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables CRMD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, CRMD 10 utilizes the atrial and ventricular sensing circuits, 382 and 384, to sense cardiac signals to determine whether a rhythm is physiologic or pathologic. As used in this section, "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 16. The data acquisition system 390 is coupled to the right atrial lead 320, the CS lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of CRMD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable CRMD 10 may be non-invasively programmed into the memory 394 through a telemetry circuit 400 in telemetric communication with the external device 20, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of CRMD 10 (as contained in the microcontroller 360 or memory 394) to be sent to the external device 20 through an established communication link 404. CRMD 10 further includes an accelerometer or other physiologic sensor or sensors 408, sometimes referred to as a "rate-responsive" sensor because it is typically used to adjust pacing stimulation rate according to the exercise state of the patient.

However, physiological sensor(s) 408 can be equipped to sense any of a variety of cardiomechanical parameters, such as heart sounds, systemic pressure, etc. As can be appreciated, at least some these sensors may be mounted outside of the housing of the device and, in many cases, will be mounted to the leads of the device. Moreover, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV delay, V-V delay, etc.) at which the atrial and ventricular pulse generators, 370 and 372, generate stimulation pulses. While shown as being included within CRMD 10, it is to be understood that the physiologic sensor 408 may also be external to CRMD 10, yet still be implanted within or carried by the patient. A common type of rate responsive sensor is an activity sensor incorporating an accelerometer or a piezoelectric crystal and/or a 3D-accelerometer capable of determining the posture within a given patient, which is mounted within the housing 340 of CRMD 10. Other types of physiologic sensors are also known, for example, sensors that sense the oxygen content of blood, respiration rate and/or minute ventilation, pH of blood, ventricular gradient, etc., The CRMD additionally includes a battery 410, which provides operating power to all of the circuits shown in FIG. 8. The battery 410 may vary depending on the capabilities of CRMD 10. If the system only provides low voltage therapy, a lithium iodine or lithium copper fluoride cell typically may be utilized. For CRMD 10, which employs shocking therapy, the battery 410 should be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, appropriate batteries are employed.

As further shown in FIG. 8, CRMD 10 is shown as having an impedance measuring circuit 412, which is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 412 is advantageously coupled to the switch 474 so that any desired electrode may be used. In particular, the impedance measurement system is configured to measure impedance along the various vectors so as to allow the CRMD to assess regional cardiac performance, as discussed above.

In the case where CRMD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules or more), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 10-40 joules or more), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Insofar as neurostimulation is concerned, the microcontroller includes a regional cardiac performance assessment system 401 operative to assess regional cardiac performance of the patient in response to neurostimulation delivered by neurostimulation leads (such as SCS leads) using techniques described above. In the example of FIG. 8, assessment system 401 includes a cardiogenic impedance vector processor 403 for processing impedance data measured along various vectors to extract pertinent fiducial point data, and a cardiac performance processor 405 for processing the extracted data to assess regional cardiac performance using the techniques described above. The microcontroller also includes a regional cardiac performance-based neurostimulation controller 407 operative to control neurostimulation in response to the assessment of regional cardiac performance within the patient by, for example, determining preferred or optimal neuromodulation parameters and then controlling the SCS system (implanted separately from the CRMD) to use the selected neuromodulation parameters. In some examples, rather than having an SCS system implanted separately from the CRMD (such as system 16 of FIG. 1), the CRMD itself includes a SCS controller 409 for directly controlling SCS leads (such as lead 18 of FIG. 1) via SCS terminal 359.

CRT pacing can be controlled using a CRT controller 411. Any diagnostic data pertinent to CRT, neuromodulation, regional cardiac performance or other matters can be stored in memory 394 under the control of diagnostic controller 413 for eventual transmission to an external system. Controller 413 also controls the generation of warning signals via warning device 421, which may be, e.g., a vibrational device or a "tickle" voltage warning device.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like. Also, it should be understood that at least some of the procedures or functions described herein might be performed by a device external to the patient, such as a bedside monitor or device programmer, based on data or signals transmitted from the implanted system. As one example, the assessment of cardiac performance may be performed by the external system based on IEGM data and impedance data sent from the implantable system. The external system then sends suitable control signals to the implantable system for controlling further neurostimulation. Hence, it should be understood that external system 20 might include suitable versions of the regional cardiac performance assessment system or the regional cardiac performance-based neurostimulation controller.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical system for implant within a patient, the method comprising:
   delivering neurostimulation to the patient;
   assessing regional cardiac performance within the patient in response to the neurostimulation, wherein assessing regional cardiac performance within the patient includes measuring a plurality of cardiogenic impedance signals along a corresponding plurality of impedance vectors; and
   controlling the delivery of additional neurostimulation based, at least in part, on the regional cardiac performance.

2. The method of claim 1 wherein the plurality of vectors include one or more of: a large field vector; a narrow field vector; a bipolar vector; a tripolar vector; and a quadpolar vector.

3. The method of claim 2 wherein the large field vector is a right ventricular (RV) coil-device can vector.

4. The method of claim 2 wherein the narrow field vector is an RV tip-RV ring vector.

5. The method of claim 1 wherein assessing regional cardiac performance includes detecting and evaluating a plurality of fiducial points within at least one cardiac cycle within each of the plurality of cardiogenic impedance signals.

6. The method of claim 5 wherein the plurality of fiducial points includes one of more of: a maximum of the cardiogenic impedance signal (Zc max); a minimum of the cardiogenic impedance signal (Zc min); a maximum rate of change of the cardiogenic signal (dZc/dt max) and a minimum rate of change of the cardiogenic signal (dZc/dt min).

7. The method of claim 5 wherein assessing regional cardiac performance includes assessing a degree of homogeneity in changes in the fiducial points of the cardiogenic impedance signals and wherein the delivery of additional neurostimulation is controlled to increase the degree of homogeneity.

8. The method of claim 5 wherein assessing regional cardiac performance includes assessing a degree of homogeneity in one or more of deltas and timings in dZc/dt-based fiducial points and wherein the delivery of additional neurostimulation is controlled to increase one or more of the deltas and the timings in the dZc/dt-based fiducial points.

9. The method of claim 1 wherein assessing regional cardiac performance includes assessing a correlation among the plurality of cardiogenic impedance signals and wherein the delivery of additional neurostimulation is controlled to improve the correlation.

10. The method of claim 1 wherein assessing regional cardiac performance includes assessing electromechanical delays among the plurality of cardiogenic impedance signals and wherein the delivery of additional neurostimulation is controlled to reduce electromechanical delays.

11. The method of claim 1 wherein assessing regional cardiac performance includes assessing differences between fiducial points within the cardiogenic impedance signals and corresponding fiducial points within one or more intracardiac electrogram (IEGM) signals and wherein the delivery of additional neurostimulation is controlled to reduce the differences therebetween.

12. The method of claim 1 wherein assessing regional cardiac performance includes assessing cardiac dyssynchrony within the plurality of cardiogenic impedance signals and wherein the delivery of additional neurostimulation is controlled to reduce dyssynchrony.

13. The method of claim 1 wherein evaluating regional cardiac performance includes assessing cardiac output based on the cardiogenic impedance signals and wherein the delivery of additional neurostimulation is controlled to increase cardiac output.

14. The method of claim 1 wherein assessing regional cardiac performance includes generating data arrays representative of changes in regional cardiac performance and corresponding changes in neurostimulation control parameters.

15. The method of claim 1 further including detecting one or more of patient posture and diurnal status and wherein the delivery of additional neurostimulation is further controlled based, at least in part, on one or more of posture and diurnal status.

16. The method of claim 1 wherein the implantable medical system includes a cardiac rhythm management device (CRMD) and a separate neurostimulation device and wherein neurostimulation is delivered by the neurostimulation device while regional cardiac performance is assessed by the CRMD.

17. The method of claim 1 wherein the implantable medical system includes CRMD equipped to directly control neurostimulation and wherein neurostimulation is delivered under the control of the CRMD while regional cardiac performance is assessed by the CRMD.

18. The method of claim 1 wherein at least some of the steps are performed by an external device based on signals received from the implantable medical system.

19. The method of claim 1 wherein neurostimulation is delivered while adjusting one or more of: a neuromodulation amplitude; a neuromodulation frequency; a neuromodulation pulse width; a neuromodulation electrode configuration and a neuromodulation duration.

\* \* \* \* \*